(12) United States Patent
Hampton et al.

(10) Patent No.: US 6,648,833 B2
(45) Date of Patent: Nov. 18, 2003

(54) RESPIRATORY ANALYSIS WITH CAPNOGRAPHY

(76) Inventors: David R. Hampton, 18130 NE. 154th St., Woodinville, WA (US) 98072; Baruch S. Krauss, 53 Addington Rd., Brookline, MA (US) 02445

(*) Notice: Subject to any disclaimer, the term of this patent is extended or adjusted under 35 U.S.C. 154(b) by 0 days.

(21) Appl. No.: 09/978,831

(22) Filed: Oct. 15, 2001

(65) Prior Publication Data

US 2003/0073919 A1 Apr. 17, 2003

(51) Int. Cl.[7] .............................................. A61B 5/00
(52) U.S. Cl. ........................... 600/532; 73/23.3; 422/84
(58) Field of Search ........................ 600/532; 73/23.3; 422/84

(56) References Cited

U.S. PATENT DOCUMENTS

| | | |
|---|---|---|
| 3,687,130 A | 8/1972 | McCormick |
| 4,169,465 A | 10/1979 | Walls et al. |
| 4,772,559 A | 9/1988 | Preti et al. |
| 4,796,639 A | 1/1989 | Snow et al. |
| 4,821,736 A | 4/1989 | Watson |
| 5,058,601 A | 10/1991 | Riker |
| 5,159,935 A | 11/1992 | Sackner et al. |
| 5,515,859 A | 5/1996 | Paz |
| 5,632,281 A | 5/1997 | Rayburn |
| 5,682,877 A | 11/1997 | Mondry |
| 5,800,361 A | 9/1998 | Rayburn |
| 5,971,934 A | 10/1999 | Scherer et al. |
| 5,984,872 A | 11/1999 | Vriend |
| 6,044,843 A | 4/2000 | O'Neil et al. |
| 6,066,101 A | 5/2000 | Johnson et al. |
| 6,068,602 A | 5/2000 | Tham et al. |
| 6,102,868 A | 8/2000 | Banner et al. |
| 6,142,952 A | 11/2000 | Behbehani et al. |
| 6,174,289 B1 | 1/2001 | Binder |
| 6,251,082 B1 | 6/2001 | Rayburn |

FOREIGN PATENT DOCUMENTS

| | | |
|---|---|---|
| DE | 28 12 379 A1 | 3/1978 |
| EP | 0 699 414 A1 | 3/1996 |

OTHER PUBLICATIONS www.emedicine.com online article on restrictive lung disease—update Jan. 20, 2003, author Sat Sharma, Editor Laurie Robin Grier, 30 pages.*
C.V. Egleston et al., "Capnography for monitoring non–intubated spontaneously breathing patients in an emergency room setting", vol. 14, No. 4, Jul. 1997, pp. 222–224, Journal of Accident and Emergency Medicine.
Brown et al., "Can Quantitative Capnometry Differentiate Between Cardiac and Obstructive Causes of Respiratory Distress?", Chest 113(2), pp. 323–326 (1998).
Yaron et al., "Utility of the Expiratory Capnogram in the Assessment of Bronchospasm," Annals of Emergency Medicine 28(4), pp. 403–407 (1996).
You et al., "Expiratory Capnography in Asthma: Evaluation of Various Shape Indices," The European Respiratory Journal 7(2), pp. 318,323 (1994).
U.S. patent application Ser. No. 09/590,202, filed Jun. 8, 2000.
U.S. Provisional Application Ser. No. 60/251,829, filed Dec. 7, 2000.
PCT Application Serial No. PCT/IL01/01127, filed Dec. 6, 2001.

* cited by examiner

Primary Examiner—Robert L. Nasser
(74) Attorney, Agent, or Firm—Shumaker & Sieffert, P.A.

(57) ABSTRACT

The invention presents techniques for identifying and guiding treatment for medical conditions, based upon the carbon dioxide concentration in the patient's breath. In an exemplary application, the techniques of the invention may be used to distinguish obstructive lung disease from restrictive lung disease, even though the symptoms of the conditions are similar. The techniques of the invention may further be used to monitor the effectiveness of the treatment.

42 Claims, 5 Drawing Sheets

RESPIRATORY ANALYSIS WITH CAPNOGRAPHY

TECHNICAL FIELD

The invention relates to medical devices, and in particular, to medical devices used to guide diagnosis, monitoring and/or treatment of respiratory conditions.

BACKGROUND

Every day, patients with difficulty breathing seek medical help. In such cases, the patients may complain of shortness of breath, but may have no idea as to the cause of the condition. Many cases of shortness of breath fall into two general categories of respiratory disorders.

One category of respiratory disorder that may cause shortness of breath is obstructive lung disease. A patient with obstructive lung disease suffers from a narrowing of the airways leading to the alveoli in the lungs. This narrowing, often caused by inflammatory reactions, results in a reduction of the patient's ability to ventilate the alveoli, because the narrowed airways reduce the maximum velocity of flow through the airways. Chronic obstructive pulmonary diseases such as asthma, bronchitis and emphysema, are some of the disorders that can cause narrowing of the airway.

A second category of respiratory disorder that may cause shortness of breath is restrictive lung disease. Restrictive lung disease is characterized by a reduction of the overall gas-exchange area in the lungs. A restrictive lung disease may be temporary, such as a short-term filling of the alveoli with fluid, or more long-lasting, such as fibrosis that prevents the alveoli from expanding during inhalation. A restrictive lung disease may also be caused by congestive heart failure leading to pulmonary edema.

When a patient complains of difficulty breathing, it is difficult for health care professionals to rapidly determine whether the problem is due to obstructive or restrictive origins. The symptoms caused by both conditions are similar. The patient's medical history may be of no help, or the patient may be incapable of giving a medical history due to age or a language barrier.

To make a reliable diagnosis of obstructive lung disease or restrictive lung disease, physicians often employ a spirometer. A spirometer is a device that measures the flow and volume of air breathed in and out. The patient breathes into the device at the direction of a health professional. The measurements recorded in a spirogram can be used to distinguish obstructive lung disease from restrictive lung disease.

There are, however, drawbacks to spirometry. First, spirometers are rarely available to health professionals treating a patient away from a hospital. Many emergency medical professionals are not trained in spirometry. Getting the patient to a spirometer and to a health professional trained in spirometry often takes time, and the patient's need for treatment may be urgent. Breathing difficulties can be life-threatening if not diagnosed accurately and treated promptly.

Second, a proper spirogram requires the patient to exert effort to follow the directions of the health professional, such as directions to inhale as much air as possible, to exhale as hard as possible and to expel as much breath as possible. Patients that are short of breath may be incapable of following the directions. Young children also have difficulty with the effort-dependent system.

Because obstructive lung disease and restrictive lung disease are treated with different methods and different medicines, distinguishing the conditions is important. Risks associated with making an incorrect diagnosis are dire. A patient who suffers from congestive heart failure but is misdiagnosed as suffering from chronic obstructive pulmonary disease, for example, may be mistakenly treated with a beta agonist. Beta agonist therapy can significantly increase myocardial oxygen consumption and worsen ischemia for that patient.

SUMMARY

In general, the invention is directed to techniques for rapidly and reliably distinguishing obstructive lung disease from restrictive lung disease. In addition, the invention is directed to techniques for monitoring the response of the patient to treatment for the condition.

To distinguish obstructive lung disease from restrictive lung disease, the invention employs measurements of the concentration of carbon dioxide in the breath of the patient. A device such as a capnograph can be used to take these measurements, and the measurements taken by the capnograph are called a capnogram. The capnograph tracks the concentration of carbon dioxide during each exhaled breath.

In a typical capnogram, the carbon dioxide concentration in the breath rises as a patient begins to exhale. The carbon dioxide concentration plateaus, then drops as the patient concludes exhalation. The shape of the curve that follows the carbon dioxide concentration is correlated to the ventilatory status of the patient. In particular, measurements of carbon dioxide concentration can be used to distinguish obstructive lung disease from restrictive lung disease.

In one embodiment, the invention is directed to a method comprising measuring a concentration of carbon dioxide in a breath expired by a patient and using this measurement to determine the presence of obstructive lung disease or restrictive lung disease. The method may take into consideration, for example, the duration of a steady rise of the concentration of carbon dioxide in the breath or the rate of increase of the concentration of carbon dioxide, as measured by the initial angle and slope of the capnogram. The method may also compare the carbon dioxide concentration in the breath with a characteristic curve. The method may further include monitoring the condition of the patient following treatment.

In another embodiment, the invention presents a device comprising a gas sensor that measures the concentration of carbon dioxide in a breath expired by a patient and a processor that determines the presence of obstructive lung disease or restrictive lung disease as a function of the measurement. The device usually includes an output device that reports the determination.

In a further embodiment, the invention presents a method comprising measuring a concentration of carbon dioxide in a breath expired by a patient and guiding treatment as a function of the measurement. Guiding treatment may include determining the presence of lung conditions, determining the severity of the conditions, and selecting medications to treat the conditions.

The invention may provide a number of advantages. For example, the invention quickly provides information to a health professional to guide treatment of the patient. In an exemplary usage, the invention rapidly and reliably distinguishes obstructive lung disease from restrictive lung disease without the need for a spirometer. Moreover, unlike a spirometer, the techniques of the invention may benefit patients that are incapable of following breathing directions. Furthermore, the invention may be small and easily portable, and may be brought to the patient by an emergency medical professional. As a result, the ventilatory status of the patient may be assessed quickly.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
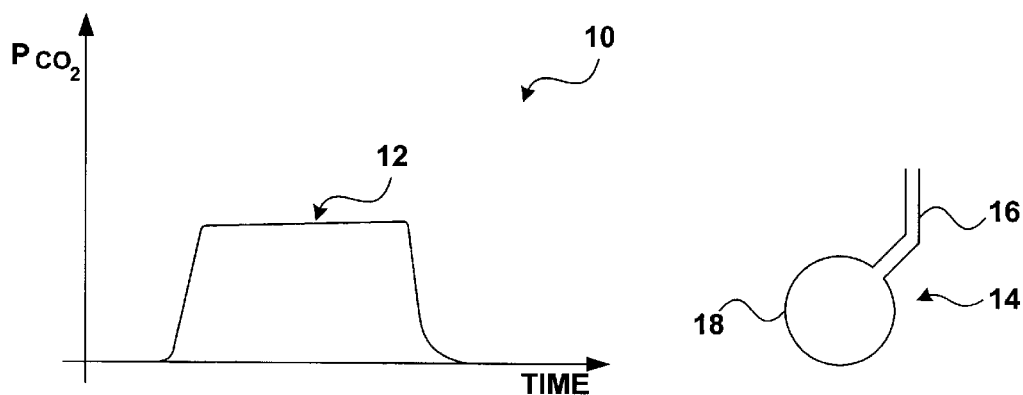
FIG. 1A includes a chart and a diagram of a capnogram and a respiratory condition of a normal patient, for comparison to FIGS. 1B and 1C.
Figure 1B:
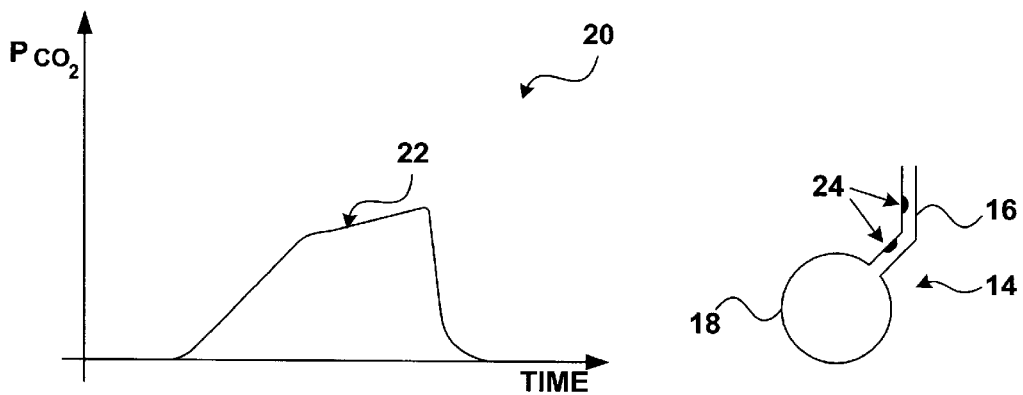
FIG. 1B includes a chart and a diagram of a capnogram and a respiratory condition of a patient with an obstructive lung disease.
Figure 1C:
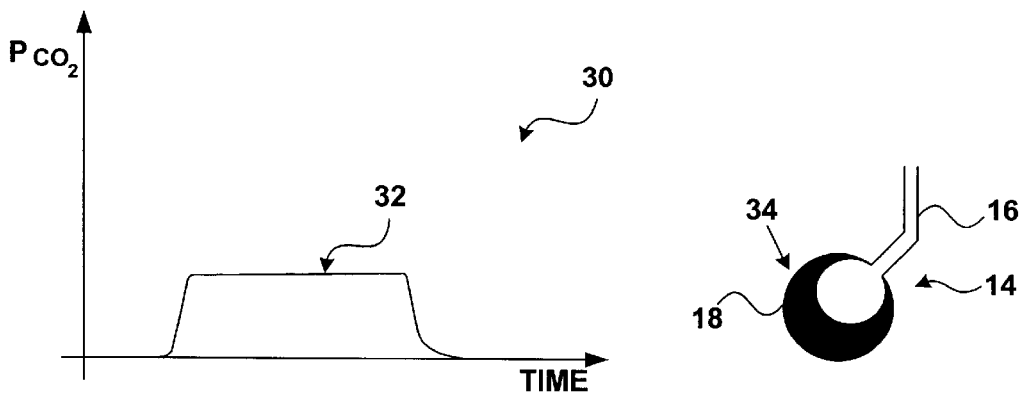
FIG. 1C includes a chart and a diagram of a capnogram and a respiratory condition of a patient with a restrictive lung disease.

FIGS. 1A, 1B and 1C show a series of three charts 10, 20 and 30, each chart accompanied by a diagram of an alveolus 14. Chart 20 shows a representative capnogram of a patient with obstructive lung disease, and chart 30 shows a representative capnogram of a patient with restrictive lung disease. Capnograms 20 and 30 are shown in reference to a capnogram 10 for a normal patient, i.e., a patient with no substantial lung disease.

The alveoli accompanying capnograms 10, 20 and 30 illustrate the nature of the condition of the patient. Each alveolus 14 includes a thin-walled inflatable sac 18 and a conducting airway 16. The alveolus accompanying capuogram 20 shows obstructions 24 in airway 16. Sac 18 may be able to expand and perform gas exchange, but expulsion of gas from sac 18 is hampered by obstructions 24, which narrow the lumen of airway 16. Obstructions 24 are characteristic of obstructive lung disease.

The alveolus accompanying capnogram 30 shows restriction 34 in sac 18, characteristic of restrictive lung disease. Restriction 34 may prevent sac 18 from expanding, or may limit the gas exchange performed by sac 18. Airway 16 is clear, allowing unimpeded expulsion of breath, but restriction 34 limits the volume of gas in the breath.

Capnograms 10, 20 and 30 include tracings 12, 22 and 32, which plot the measured concentration of carbon dioxide in the breath as a function of time. Each tracing 12, 22 and 32 shows the concentration of carbon dioxide rise, reach a plateau and drop. The shapes of tracings 12, 22 and 32, however, are different. As will be shown in more detail below, analysis of the shapes of tracings 22 and 32 may be used to distinguish obstructive lung disease from restrictive lung disease.

Tracing 22 from a patient with obstructive lung disease shows a more gradual rise in the ascending slope of the carbon dioxide concentration, as compared with tracings 12 and 32 from a normal patient and a patient with restrictive lung disease, respectively. The more gradual rise is caused by the inability of the patient to exhale rapidly due to obstructions 24. The patient ventilates adequately because sac 18 is clear, but the patient is not able easily to expel the contents of sac 18 through airway 16.

The ascending slope of tracing 32 from a patient with restrictive lung disease shows a rapid rise in carbon dioxide concentration when compared with tracing 22, but a nearly normal rise in carbon dioxide concentration when compared with tracing 12. A patient with restrictive lung disease has restriction 34 in sac 18 but no obstructions to prevent exhalation of carbon dioxide, so the rise in carbon dioxide concentration is initially normal, or nearly so. The carbon dioxide concentration in tracing 32, however, plateaus at a lower concentration when compared to tracings 12 and 22, indicating that the patient is less adequately ventilated than the normal patient and the patient with obstructive lung disease.

Figure 2A:
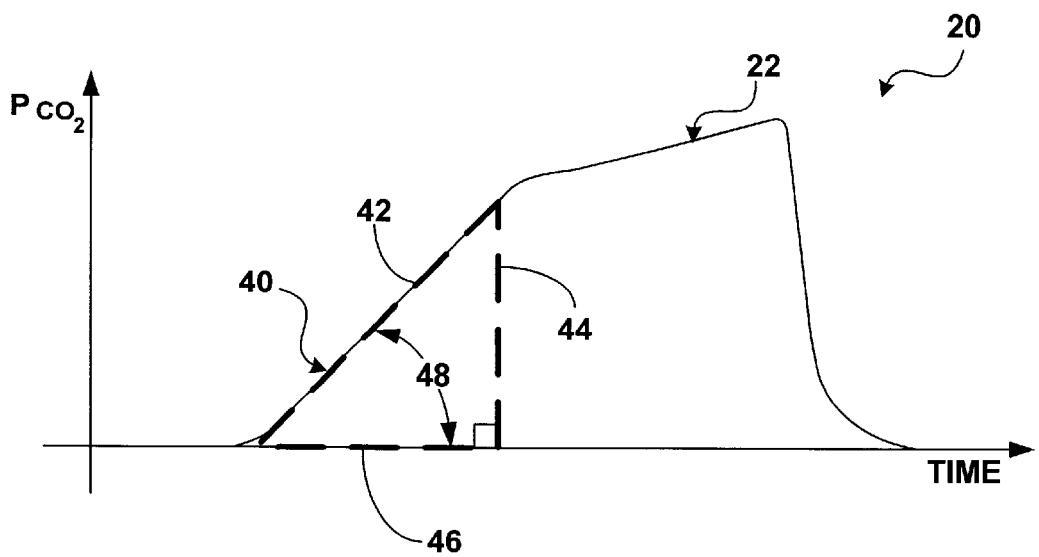
FIG. 2A includes a chart of a capnogram of a patient with an obstructive lung disease.
Figure 2B:
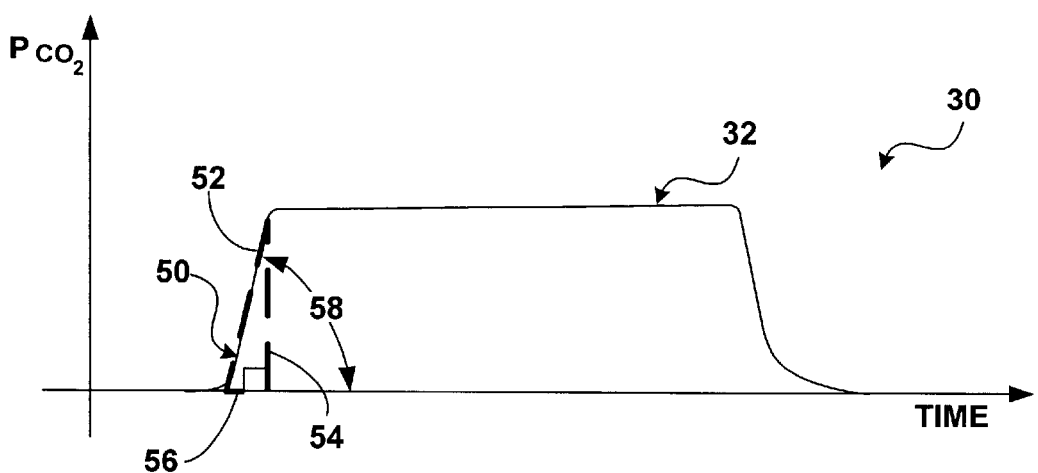
FIG. 2B includes a chart of a capnogram of a patient with a restrictive lung disease.

FIGS. 2A and 2B provide a more detailed analysis of capnograms 20 and 30. When a patient first begins to exhale, the carbon dioxide concentration in the first part of the breath is negligible. The first exhaled gases generally carry air from so-called "dead space," i.e., the trachea, bronchi and other structures in the brigs in which no gas exchange takes place. In a typical patient, the volume of the dead space is approximately 150 mL. As gases from alveoli are expelled with air from the dead space, the concentration of carbon dioxide in the breath rises. When the dead space gases are mostly expelled, the concentration of carbon dioxide begins to reach a plateau. The plateau is typically not flat.

Once the concentration of carbon dioxide in the breath begins to rise, the rise in concentration may be approximated by a straight line. The straight line may form the hypotenuse of a right triangle. In tracing 22, the rise of carbon dioxide concentration is approximated by hypotenuse 42 of right triangle 40, and in tracing 32, the rise of carbon dioxide concentration is approximated by hypotenuse 52 of right triangle 50.

Base 46 of triangle 40 represents the duration of the rise of carbon dioxide concentration, i.e., the approximate time it takes for the carbon dioxide concentration in the breath of a patient with obstructive lung disease to reach a plateau. Height 44 of triangle 40 represents the concentration of carbon dioxide when the patient reaches the plateau. Likewise, for a patient with restrictive lung disease, base 56 represents the duration of the rise of carbon dioxide concentration, and height 54 represents the concentration of carbon dioxide when the patient reaches the plateau.

Many of the quantities are related, and other quantities can be derived, by the application of trigonometry. For example, the areas of triangles 40 and 50 can be computed and the lengths of hypotenuses 42 and 52 can be determined. The rate of increase of carbon dioxide concentration can also be determined by taking the derivative of the beginning of tracings 22 and 32, which gives the slope.

Moreover, take-off angles 48 and 58 can be found. Take-off angles 48 and 58 are one measure of the slope of hypotenuses 42 and 52, and are a function of how rapidly carbon dioxide concentration in the breath rises. Although take-off angles 48 and 58 can be derived by trigonometry from other measurements, take-off angles 48 and 58 can also be measured directly, independent of other parameters.

As shown by tracing 22, a patient with obstructive lung disease takes a longer time than a patient with restrictive lung disease to expel dead space air. This is shown by the more gradual slope of hypotenuse 42, as compared to hypotenuse 52. The gradual slope of hypotenuse 42 is indicative of obstructive lung disease because the gradual slope represents that it takes longer for the patient to move carbon dioxide-rich gas from his alveoli.

By contrast, the slope of hypotenuse 52 is considerably steeper than hypotenuse 42. The steep slope of hypotenuse 52 is not indicative of obstructive lung disease because it suggests a rapid expulsion of carbon dioxide-rich gas from the alveoli. The extent of hypotenuse 52, height 54 and base 56 are small, however, when compared to the counterparts of triangle 40. Another measure of the difference is the area of triangle 50, which is considerably smaller than the area of triangle 40. The smaller area of triangle 50 is indicative of restrictive lung disease because the patient suffers from restricted gas exchange, and cannot expel as large a volume of carbon dioxide-rich gas from the alveoli.

Applying analysis techniques such as those described above, the initial carbon dioxide concentration in the exhalation of a patient can be used to distinguish obstructive lung disease from restrictive lung disease. A patient with obstructive lung disease expels carbon dioxide more slowly, but in greater volume, than a patient with restrictive lung disease.

Importantly, capnograms 20 and 30 need not be effort-dependent. Unlike spirograms, in which the patient must follow a set of instructions, capnograms 20 and 30 may be taken while the patient is breathing as comfortably as he is able, without requiring the patient to follow any breathing instructions. The clarity of tracings 22 and 32 may be improved if the patient is able to follow simple breathing instructions from a health professional, but following the instructions is not essential to the invention.

Figure 3:
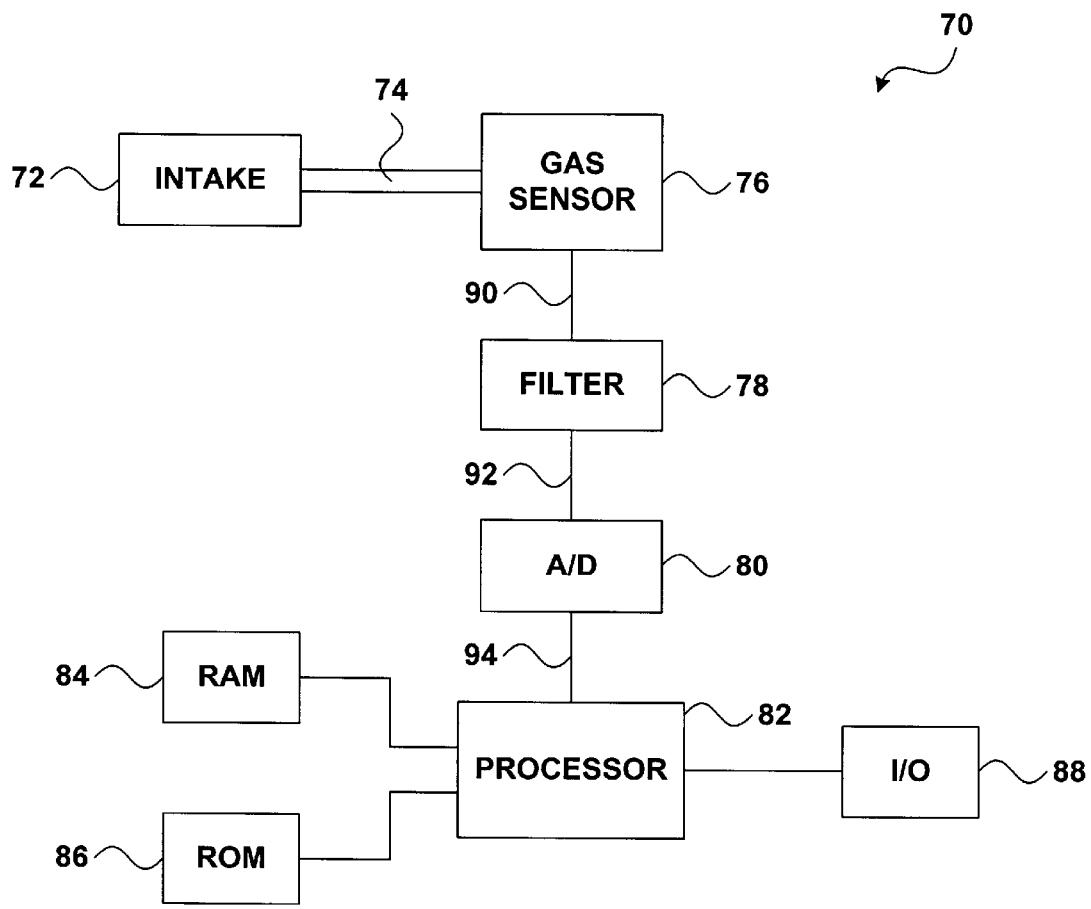
FIG. 3 is a block diagram of an apparatus that is one embodiment of the invention.

FIG. 3 is a block diagram of a system 70 that may be used to practice the invention. System 70 includes intake apparatus 72. The patient exhales into intake apparatus 72, which may be an apparatus such as a nasal cannula or a mask. The exhalation from the patient passes through tube 74 to gas sensor 76, which measures the concentration of carbon dioxide in the breath. Gas sensor 76 may be part of a capnograph. Gas sensor 76 may measure carbon dioxide concentration using techniques such as infrared detection, which can track changes in concentration in real time.

Gas sensor 76 passes measurements 90 to low-pass filter 78, which prevents aliasing. Filter 78 passes filtered measurements 92 to analog-to-digital converter 80, which converts filtered analog measurements 92 to digital measurement data 94. Processor 82 receives digital measurement data 94. Digital measurement data 94 may be stored in random access memory (RAM) 84.

Based upon digital measurement data 94, processor 82 evaluates the carbon dioxide concentration in the patient's breath over time. Processor 82 may, for example, construct tracings such as tracings 22 or 32 shown in FIGS. 2A and 2B, and derive triangles such as triangles 40 or 50. Processor 82 may find quantities such as duration of the rise of carbon dioxide concentration or take-off angle. Using quantities such as these, processor 82 may determine whether the data support a diagnosis of obstructive lung disease or restrictive lung disease.

Processor 82 may, for example, measuring the duration of a steady rise of the concentration of carbon dioxide. A long duration is indicative of obstructive lung disease and a short duration is indicative of restrictive lung disease. Accordingly, processor 82 may determine that the patient probably suffers from obstructive lung disease when the duration is longer than a threshold duration, and may determine that the patient probably suffers from restrictive lung disease when the duration is shorter than the threshold duration.

In addition or in the alternative, processor 82 may measure the rate of increase of the concentration of carbon dioxide. The rate of increase may be quantified by, for example, the steepness of the hypotenuse of the ascending slope, or by the magnitude of the take-off angle, or both. Processor 82 may determine that the patient probably suffers from obstructive lung disease when the rate of increase is lower than a threshold rate, and may determine that the patient probably suffers from restrictive lung disease when the rate of increase is higher than the threshold rate.

As an alternative to or in addition to this analysis, processor 82 may compare digital measurement data 94 to one or more characteristic curves. Memory such as read-only memory (ROM) 86 may store data that are characteristic of obstructive lung disease and data that are characteristic of restrictive lung disease. Processor 82 may correlate the measurements of the concentration of carbon dioxide from the patient with the characteristic curves. When the correlation exceeds a preselected threshold value, processor 82 may determine that the data support a diagnosis of obstructive lung disease or restrictive lung disease.

In addition to determining whether the patient more likely suffers from obstructive lung disease or restrictive lung disease, processor 82 may also gauge the severity of the condition. Processor 82 may report a severe case of obstructive lung disease, for example, when take-off angle 48 is below a particular value, indicating that the patient has extreme difficulty pushing out his breath. Degrees of severity may also be reported, such as "critical," "moderate" and "mild."

Processor 82 reports the results of the analysis to the health professional via input/output (I/O) device 88. I/O device 88 may include, for example, a display screen that displays text or graphics, or a collection of light emitting diodes. Processor 82 may report an analysis, such as "Patient's exhaled carbon dioxide concentration indicates a greater likelihood of obstructive lung disease than restrictive lung disease," or "Patient's exhaled carbon dioxide concentration indicates a high probability of obstructive lung disease." Processor 82 may further report on the severity of the condition, and/or may display the tracing of the carbon dioxide concentration. Furthermore, processor 82 may suggest an appropriate treatment based upon the analysis.

In contrast to a spirometer, system 70 may be small and easily portable. Accordingly, system 70 may be included in first aid packages in public venues such as airports and health clubs, or may be carried to the patient by an emergency medical professional. Furthermore, unlike a spirometer, system 70 may provide guidance for treatment of the patient very quickly, and need not be effort-dependent.

The organization of system 70 is an example of one system that may be used to practice the invention, and the invention is not limited to the system shown. For example, digital measurement data 94 may be supplied to RAM 84 via a direct memory access module (not shown in FIG. 3), rather than via processor 82. ROM 86 may include erasable programmable read-only memory (EPROM). I/O device 88 may be one of several input and/or output devices. The invention encompasses all of these variations.

Figure 4:
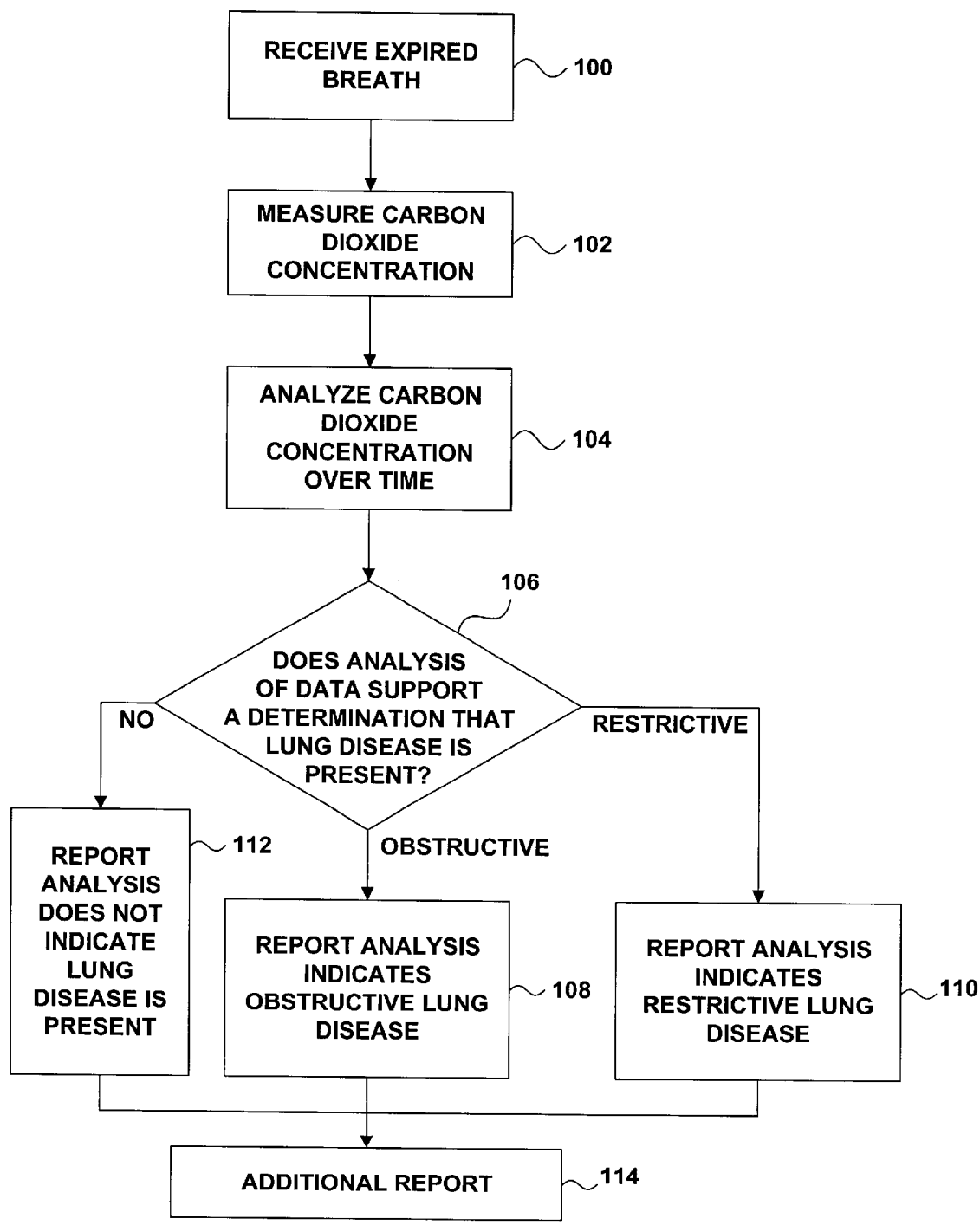
FIG. 4 is a flow diagram illustrating techniques for using capnography to analyze respiratory conditions.

FIG. 4 is a flow diagram illustrating an embodiment of the invention in an exemplary application, such as the case of a patient suffering from a shortness of breath. System 70 receives expired breath from the patient via intake apparatus 72 (100). Gas sensor 76 measures the carbon dioxide concentration (102) and reports the measurements to processor 82.

In addition to making measurements of carbon dioxide concentration, system 70 helps in determine the nature of the condition and further helps guide treatment of the patient. In a typical application, processor 82 analyzes the measurements over time (104) using techniques such as those described above and ascertains whether the data support a determination that lung disease is present (106). When the data support a determination that obstructive lung disease is present, processor 82 may so report via I/O device 88 (108). Similarly, when the data support a determination that restrictive lung disease is present, processor 82 may so report (110). In some circumstances, the data may support neither case, and processor 82 may so report (112).

Processor 82 may also report additional information (114) that may guide the treatment of the patient. For example, processor 82 may report the severity of the condition, or may suggest a medicine for the condition, or may recommend that the measurements be repeated, or may suggest that the patient be instructed to breathe in a particular manner.

Figure 5:
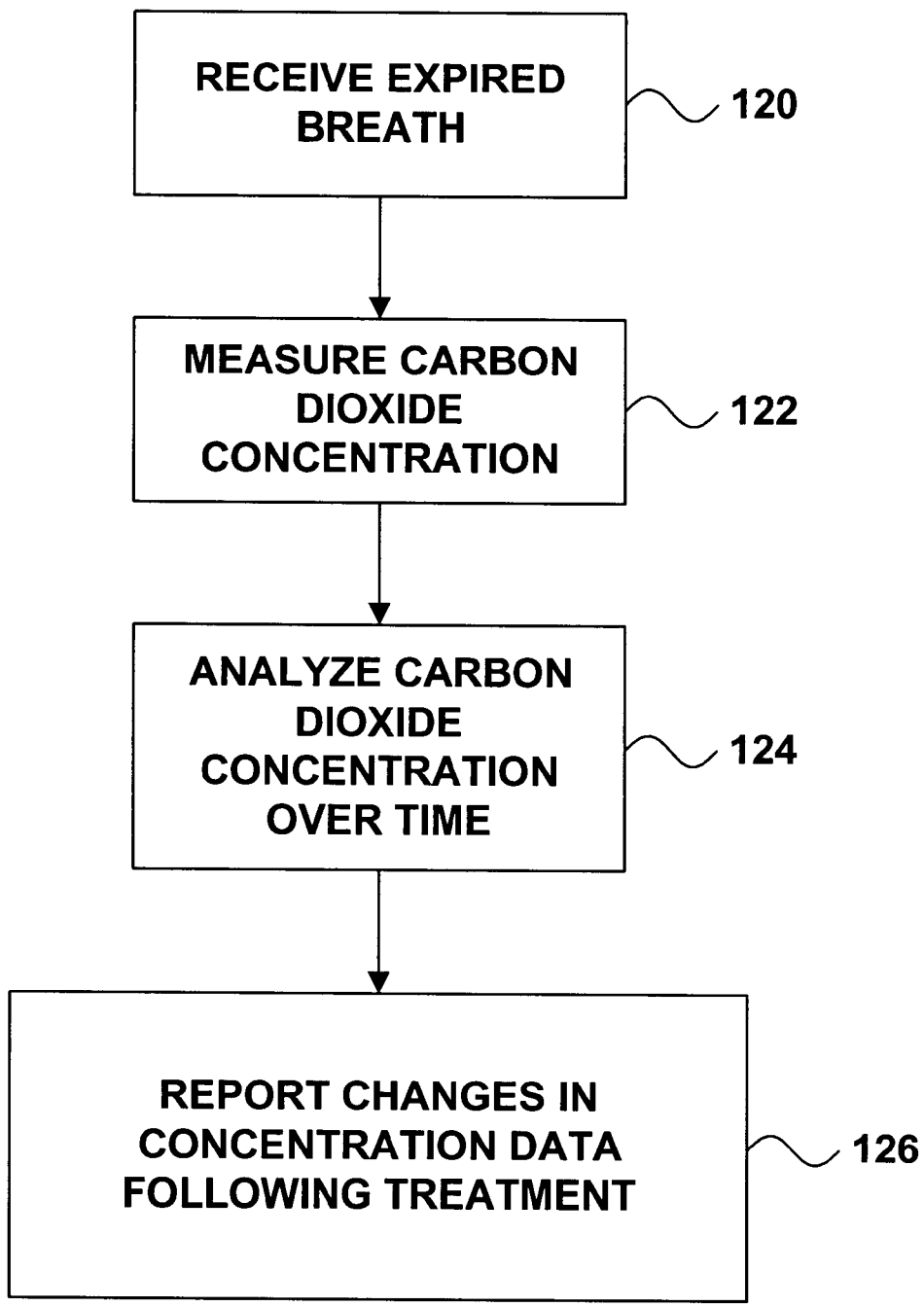
FIG. 5 is a flow diagram illustrating techniques for using capnography to monitor respiratory conditions following treatment.

FIG. 5 is a flow diagram showing how the invention may be implemented to monitor the effectiveness of treatment. In some circumstances, such as treatment of some forms of asthma, proper treatment produces a prompt improvement in the condition of the patient, and this improvement can be monitored. System 70 receives expired breath from a patient via intake apparatus 72 (120), gas sensor 76 measures the carbon dioxide concentration (122) and processor 82 analyzes the measurements (124). Instead of reporting a determination of lung disease, however, processor 82 monitors changes in the condition of the patient, and reports the changes via I/O device 88. In this way, the invention may be used to observe the responsiveness of the patient to treatment.

Various embodiments of the invention have been described. These embodiments are illustrative of the practice of the invention. Various modifications to the apparatus or methods may be made without departing from the scope of the invention. For example, the invention need not be embodied in a standalone apparatus, but may be combined with an apparatus that performs other diagnostic or treatment functions. Similarly, the invention need not be embodied in a method that analyzes only carbon dioxide concentration in the breath, but may include other diagnostic measurements such as measurements of heart rate, respiration rate, blood pressure, electrocardiogram and blood oxygenation.

Other embodiments may employ capnograms from a plurality of breaths, and may process the capnograms by techniques such as averaging. These and other embodiments are within the scope of the following claims.

What is claimed is:

1. A method comprising:
   measuring a concentration of carbon dioxide in a breath expired by a patient; and
   determining the presence of restrictive lung disease as a function of the measurement.

2. The method of claim 1, wherein measuring a concentration of carbon dioxide in a breath expired by a patient comprises generating a capnogram with a capnograph.

3. The meted of claim 1, wherein measuring the concentration of carbon dioxide in a breath expired by a patient comprises measuring the concentration of carbon dioxide as a function of time.

4. The method of claim 3, wherein determining the presence of restrictive lung disease as a function of the measurement comprises measuring the ascending slope of a curve traced by the measurements of the concentration of carbon dioxide over time.

5. The method of claim 1, further comprising determining the presence of obstructive lung disease as a function of the measurement.

6. The method of claim 5, wherein determining the presence of one of obstructive lung disease and restrictive lung disease as a function of the measurement comprises:
   measuring the duration of a steady rise of the concentration of carbon dioxide;
   determining the presence of obstructive lung disease when the duration is longer than a threshold duration; and
   determining the presence of restrictive lung disease when the duration is shorter than the threshold duration.

7. The method of claim 5, wherein determining the presence of one of obstructive lung disease and restrictive lung disease as a function of the measurement comprises:
   measuring the rate of increase of the concentration of carbon dioxide;
   determining the presence of obstructive lung disease when the rate of increase is lower than a threshold rate; and
   determining the presence of restrictive lung disease when the rate of increase is higher than the threshold rate.

8. The method of claim 5, wherein determining the presence of obstructive lung disease as a function of the measurement comprises:
   measuring the concentration of carbon dioxide as a function of time;
   comparing the measurement of the concentration of carbon dioxide as a function of time to a characteristic curve; and
   determining the presence of obstructive lung disease when the correlation of the measurement of the concentration of carbon dioxide as a function of time to the characteristic curve exceeds a threshold value.

9. The method of claim 1, further comprising reporting the determination.

10. The method of claim 1, wherein the breath expired byte patient is a first breath, the method further comprising:
    measuring a concentration of carbon dioxide in a second breath expired by the patient following treatment;
    evaluating a change in concentration of carbon dioxide between the first breath and the second breath.

11. The method of claim 10, further comprising reporting the evaluation.

12. The method of claim 1, further comprising treating the patient as a function of the determination.

13. The method of claim 1, further comprising recommending treatment of the patient as a function of the determination.

14. A device comprising:
    a gas sensor that measures the concentration of carbon dioxide in a breath expired by a patient; and
    a processor that determines the presence of restrictive lung disease as a function of the measurement.

15. The device of claim 14, further comprising an output device that reports the determination.

16. The device of claim 14, further comprising an intake apparatus that conveys the expired breath from the patient to the gas sensor.

17. The device of claim 14, further comprising an analog-to-digital converter that converts analog measurements from the gas sensor to digital values, wherein the processor analyzes the digital values to determine the presence of restrictive lung disease.

18. The device of claim 14, further comprising a capnograph that includes the gas sensor.

19. The device of claim 14, wherein the gas sensor comprises an infrared sensor.

20. The device of claim 14, wherein the processor further determines the presence of obstructive lung disease as a function of the measurement.

21. A method comprising:
measuring a first concentration of carbon dioxide in a breath expired by a patient;
guiding treatment of the patient as a function of the measurement, wherein guiding treatment comprises at least one of determining the presence of restrictive lung disease and suggesting a medicine;
measuring a second concentration of carbon dioxide in a second breath expired by the patient after a treatment; and
monitoring the response of the patient to the treatment as a function of the measurement of the second concentration.

22. The method of claim 21, wherein guiding treatment further comprises determining the presence of obstructive lung disease.

23. The method of claim 22, wherein guiding treatment further comprises assessing the severity of the obstructive lung disease.

24. The method of claim 21, wherein guiding treatment further comprises assessing the severity of the restrictive lung disease.

25. The method of claim 21, wherein measuring the concentration of carbon dioxide in the breath expired by a patient comprises measuring the concentration of carbon dioxide as a function of time.

26. The method of claim 21, further comprising reporting a recommendation for treatment.

27. An apparatus comprising:
a sensing means that measures the concentration of carbon dioxide over time in a breath expired by a patient;
a processing means that determines the presence of restrictive lung disease as a function of the measurement; and
an output means that reports the determination.

28. The apparatus of claim 27, further comprising:
a filtering means that receives a signal from the sensing means and generates a filtered signal comprising low frequency components of the signal; and
a converting means that receives the filtered signal and generates a digital signal received by the processing means.

29. The apparatus of claim 27, further comprising memory means that stores data characteristic of at least one of obstructive lung disease and restrictive lung disease.

30. The device of claim 27, wherein the processing means further determines the presence of obstructive lung disease as a function of the measurement.

31. A method comprising:
measuring a concentration of carbon dioxide in a breath expired by a patient; and
distinguishing between one of obstructive lung disease and restrictive lung disease as a function of the measurement,
wherein distinguishing between one of obstructive lung disease and restrictive lung disease as a function of the measurement comprises measuring the ascending slope of a curve traced by the measurements of the concentration of carbon dioxide over time.

32. The method of claim 31, further comprising treating the patient as a function of the distinction.

33. The method of claim 31, further comprising recommending treatment of the patient as a function of the distinction.

34. A method comprising:
measuring a concentration of carbon dioxide in a breath expired by a patient; and
determining the presence of one of obstructive lung disease and restrictive lung disease as a function of the measurement, wherein determining the presence of one of obstructive lung disease and restrictive lung disease as a function of the measurement comprises:
measuring the duration of a steady rise of the concentration of carbon dioxide;
determining the presence of obstructive lung disease when the duration is longer than a threshold duration; and
determining the presence of restrictive lung disease when the duration is shorter than the threshold duration.

35. The method of claim 34, further comprising treating the patient as a function of the determination.

36. The method of claim 34, further comprising recommending treatment of the patient as a function of the determination.

37. A method comprising:
measuring a concentration of carbon dioxide in a first breath expired by a patient;
determining the presence of one of obstructive lung disease and restrictive lung disease as a function of the measurement;
measuring a concentration of carbon dioxide in a second breath expired by the patient following treatment; and
evaluating a change in concentration of carbon dioxide between the first breath and the second breath.

38. The method of claim 37, further comprising reporting the evaluation.

39. A method comprising:
measuring a first concentration of carbon dioxide in a first breath expired by a patient;
measuring a second concentration of carbon dioxide in a second breath expired by the patient after a treatment; and
monitoring the response of the patient to the treatment as a function of the measurement of the second concentration.

40. The method of claim 39, further comprising guiding treatment of the patient as a function of the response.

41. The method of claim 40, wherein guiding treatment comprises at least one of determining the presence of restrictive lung disease, assessing the severity of the restrictive lung disease, determining the presence of obstructive lung disease, assessing the severity of the obstructive lung disease and suggesting a medicine.

42. The method of claim 39, wherein measuring the first concentration of carbon dioxide in the breath expired by a patient comprises measuring the concentration of carbon dioxide as a function of time.

* * * * *

UNITED STATES PATENT AND TRADEMARK OFFICE
CERTIFICATE OF CORRECTION

PATENT NO. : 6,648,833 B2
DATED : November 18, 2003
INVENTOR(S) : Hampton et al.

It is certified that error appears in the above-identified patent and that said Letters Patent is hereby corrected as shown below:

Title page,
Item [56], References Cited, U.S. PATENT DOCUMENTS, add the following:
-- 5,751,911   5/1998      Goldman
   6,428,483   8/2002      Carlebach --

Column 4,
Line 26, "brigs" should read --lungs --

Column 7,
Line 64, "meted" should read -- method --

Column 8,
Line 45, "byte" should read -- by the --

Signed and Sealed this

Twenty-third Day of November, 2004

JON W. DUDAS
*Director of the United States Patent and Trademark Office*